US00PP29049P3

(12) United States Plant Patent
Southwick

(10) Patent No.: US PP29,049 P3
(45) Date of Patent: Mar. 6, 2018

(54) CHERRY TREE NAMED 'SMS-9CA 2014-9'

(50) Latin Name: ***Prunus avium* L.**
Varietal Denomination: SMS-9CA 2014-9

(71) Applicant: Stephen M. Southwick, Lodi, CA (US)

(72) Inventor: Stephen M. Southwick, Lodi, CA (US)

(73) Assignee: SMS Unlimited, LLC, Lodi, CA (US)

( * ) Notice: Subject to any disclaimer, the term of this patent is extended or adjusted under 35 U.S.C. 154(b) by 3 days.

(21) Appl. No.: 14/999,843

(22) Filed: Jul. 8, 2016

(65) Prior Publication Data

US 2018/0014442 P1 Jan. 11, 2018

(51) Int. Cl.
*A01H 5/08* (2006.01)

(52) U.S. Cl.
USPC ..... Plt./181
CPC ..... *A01H 5/085* (2013.01)

(58) Field of Classification Search
USPC ..... Plt./181
CPC .... A01H 5/085; A01H 5/0216; A01H 5/0837; A01H 5/08
See application file for complete search history.

*Primary Examiner* — June Hwu
(74) *Attorney, Agent, or Firm* — Randall Danskin P.S.

(57) ABSTRACT

A new and distinct variety of sweet cherry tree, which is denominated varietally as 'SMS-9CA 2014-9', and which produces fruit having an early ripening fruit ('Chelan' timing), and which further has a large fruit, high production, self-fertility, a long stem, and strong fruit attachment, and which further has a very attractive appearance, and organoleptic qualities.

5 Drawing Sheets

Latin name: *Prunus avium* L.
Varietal denomination: SMS-9CA 2014-9.

BACKGROUND OF THE INVENTION

The new variety was discovered from an open pollination of seeds collected from a proprietary sweet cherry selection 'SC3-35' (unpatented), and which was located near Vina, Lodi, and Bakersfield, Calif. in 1998. The seeds stratified, testa removed, and then were germinated and planted in pots in 1999. After germination, the aforementioned seeds were grown in pots for 3 years until flowering. Fruit was first observed in 2002. A first asexual propagation took place when buds were taken in that same year and propagated on the *Prunus mahaleb* rootstock (unpatented) for further confidential trials, and which were conducted in Vina, Calif., and Spain starting in 2003. After two years of cropping in pots, buds were taken in a second asexual reproduction and grafted onto *Prunus mahaleb* rootstock for further evaluation in Stockton, Calif. in 2004. Additional confidential trials similar to that which are described, above, were conducted starting in 2006 in Stockton, Calif., and in 2009 in Roosevelt, Wash. In 2007, the first fruit from trial growing fields were then evaluated.

Throughout the aforementioned trials and various asexual propagations, the tree and fruit produced thereby were compared to the originally discovered plant. All characteristics of the original tree, and its fruit were established, and appears to have been transmitted to the aforementioned succeeding generations.

SUMMARY OF THE INVENTION

The variety 'SMS-9CA 2014-9' is an early ripening cherry tree selection which matures with or slightly after the 'PC 7146-23' cherry tree variety (U.S. Plant Pat. No. 8,545, hereinafter referred to by its trade name 'Chelan') in Washington State; and with or slightly later than the 'Brooks' Cherry Tree (U.S. Plant Pat. No. 6,676) which are growing in California. 'SMS-9CA 2014-9' is distinct from the aforementioned, well known varieties because the fruit it produces is larger, and the tree is more productive than either the 'Chelan' or 'Brooks' Cherry trees. It is believed that the self-fertile alleles $S_1S_4$, help to insure regular cropping as compared with the self-infertile Cherry cultivars 'Chelan' and 'Brooks' which require cross-pollination. The organoleptic qualities of the fruit are superior to the fruit produced by 'Chelan' as well, and is highly appreciated by those consuming the fruit. The fruit size can average 25-28 mm in diameter as compared with 22-24 mm for the fruit produced by 'Chelan' Cherry Tree even though the crop is much larger. Many fruit of the new variety can be in the 32 to 36 mm size range. The fruit produced by the 'Chelan' Cherry tree reached harvest maturity in the first to second week of May under the ecological conditions prevailing near Stockton Calif. The cherry of the new variety is dark red (CTIFL, color codes 4 and 5) (Centre Technique Interprofessional des fruit et legumes) at harvest, and a deep purplish color (CTIFL 6 color code) at full maturity. The firmness of the fruit is comparable to the fruit of the 'Chelan' Cherry Tree with a tendency toward being slightly less firm because of the large cropping potential of the new variety.

The present, new variety is distinguishable from the 'SC3-35' cherry tree variety (the parent), in view of its higher and more regular fruit production per tree, when compared to the fruit production of the 'SC3-35' cherry tree. Further, the present, new variety is distinguishable from the 'SC3-35' cherry tree in view of the fruit it produces, which possesses a larger fruit size than the fruit produced by the 'SC3-35' cherry tree. Still further, the present, new variety is distinguishable from the 'SC3-35' cherry tree (the parent) in view of the fruit it produces, which possesses an earlier ripening date than the fruit produced by the 'SC3-35' cherry tree. Moreover, the present, new variety is distinguishable from the 'SC3-35' cherry tree (the parent) in view of the fruit it produces, which possesses longer stem length relative to the fruit produced by the 'SC3-35' cherry tree.

BRIEF DESCRIPTION OF THE DRAWINGS

The accompanying drawings, which are provided are color photographs of the new Cherry Tree variety.

Figure 1:
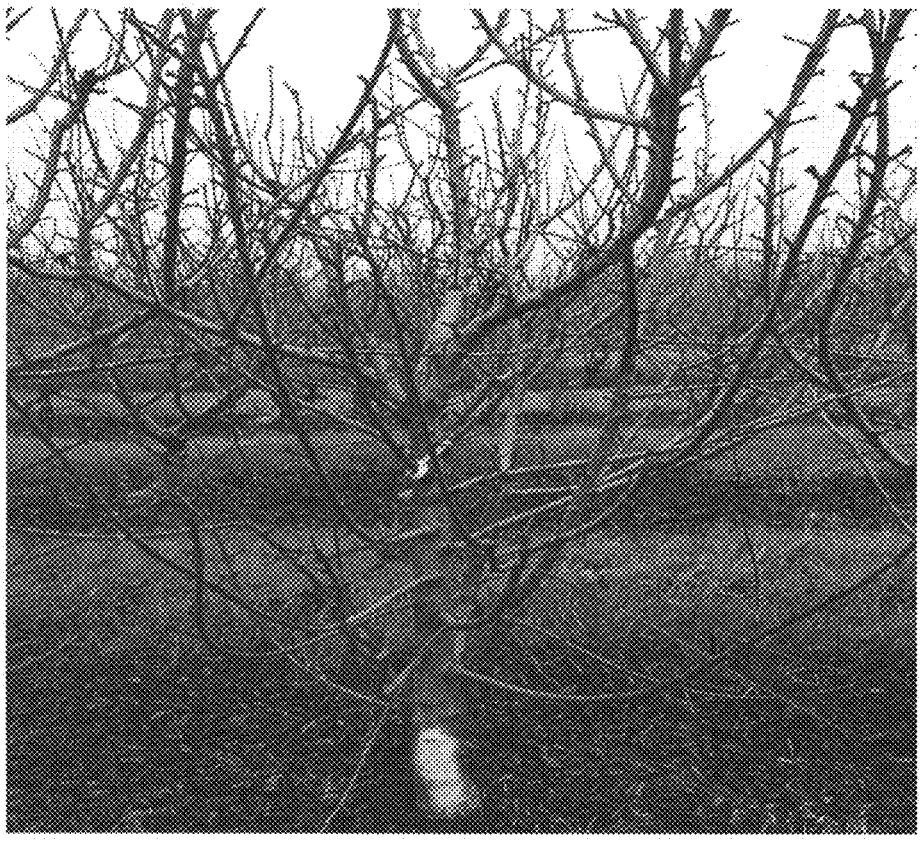
FIG. 1 depicts the original tree shown at full dormancy. This photograph depicts the original tree at 10 years of age.
Figure 2:
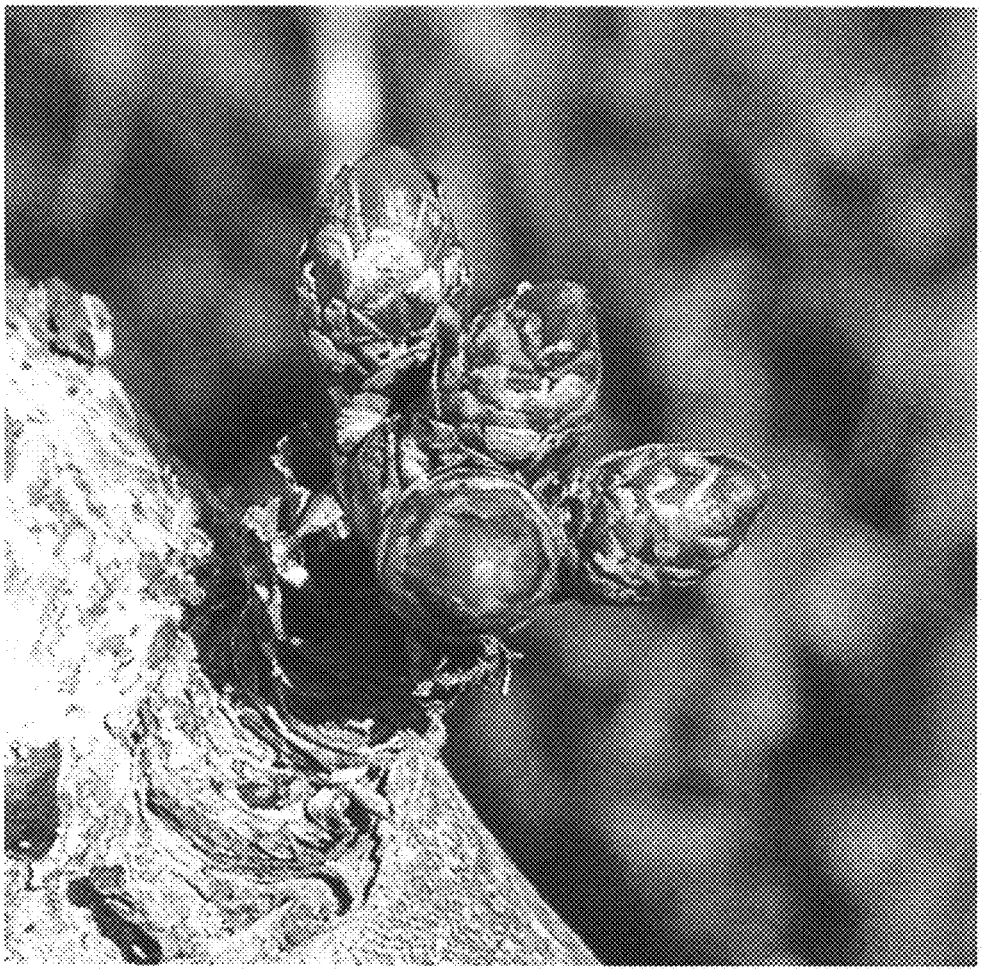
FIG. 2 depicts a semi-dormant fruit spur of the new tree.
Figure 3:
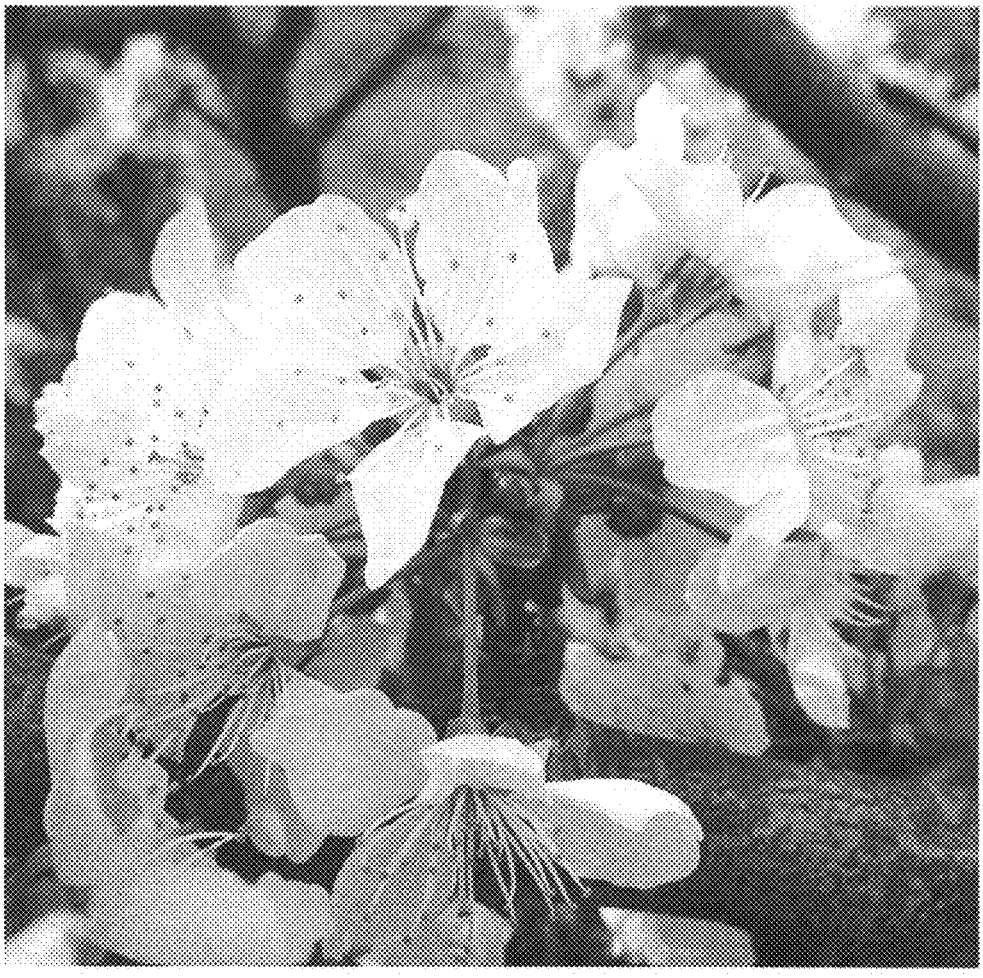
FIG. 3 depicts the flowering and blossom characteristics of the new tree.
Figure 4:
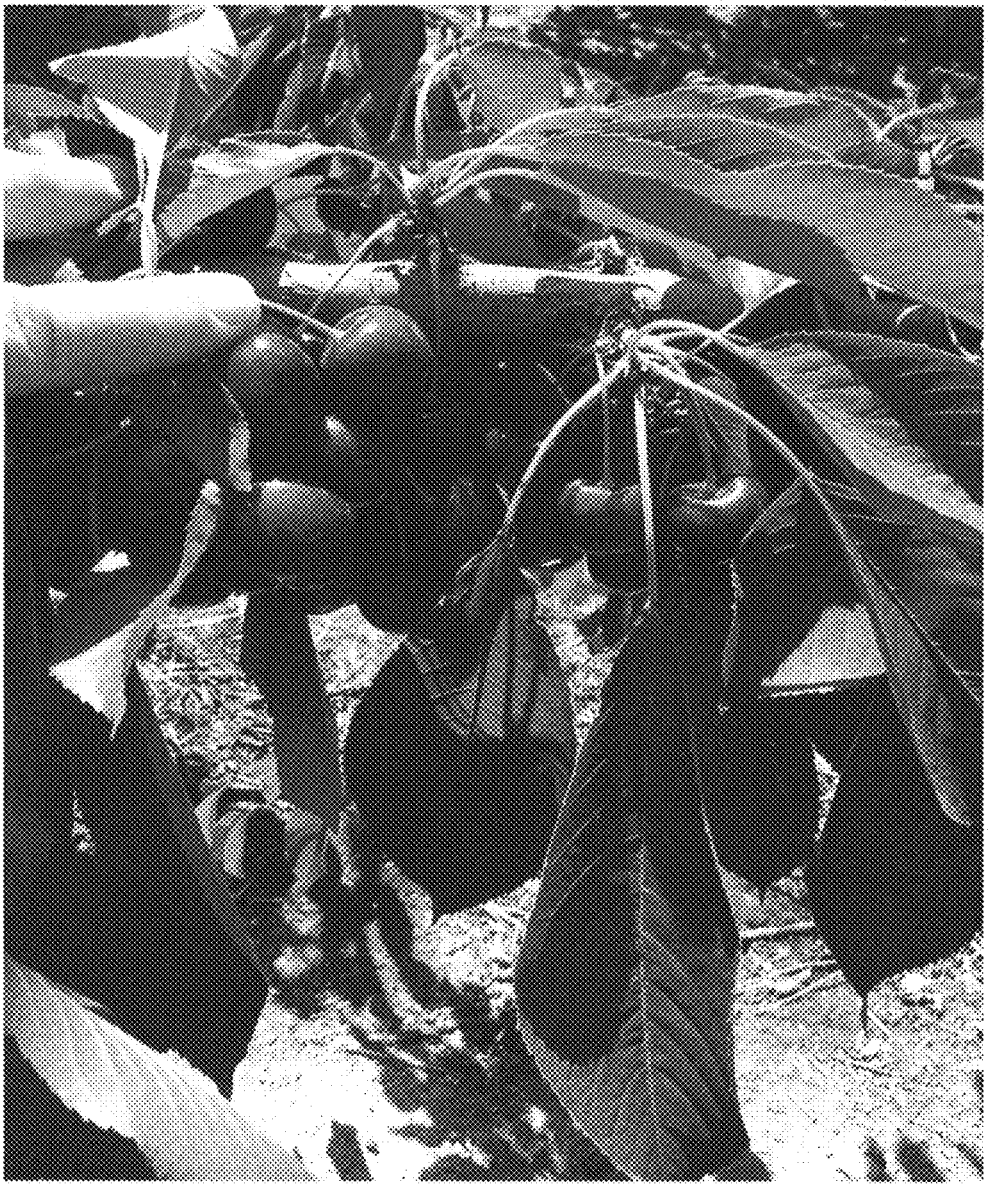
FIG. 4 depicts the fruiting characteristics of the new tree.
Figure 5:
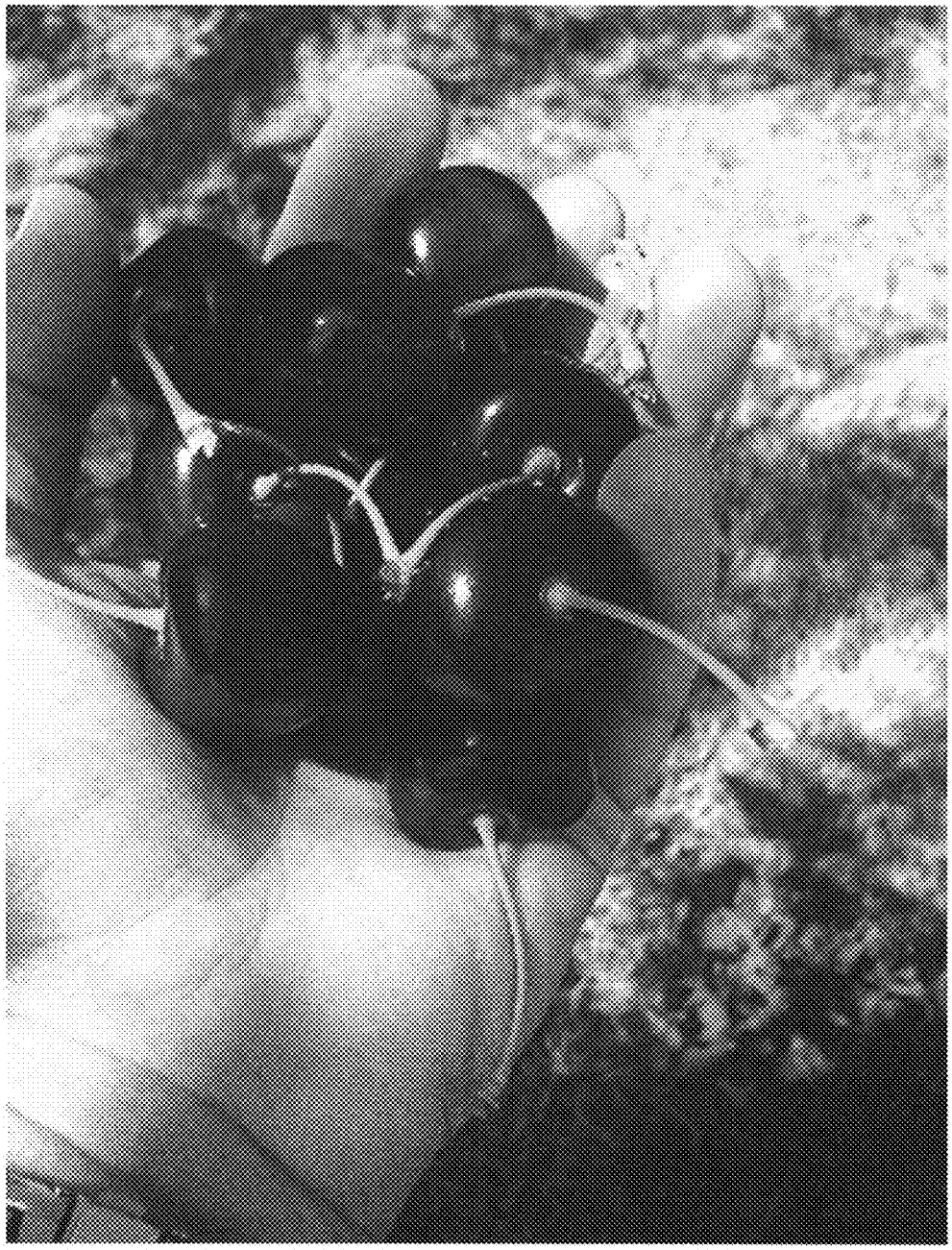
FIG. 5 depicts the exterior appearance of the fruit produced by the parent tree at harvest and the typical foliage which is seen.

The colors in these photographs are as nearly true as is reasonably possible in a color representation of this type. Due to chemical development processing, printing and the like, the leaves, fruit, flowers, and other parts of the plant, which are depicted in the enclosed photographs may, or may not be accurate when compared to the actual specimens. For this reason future color references should be made to the color plates (Royal Horticulture Society 4$^{th}$ Edition 2001) and the description provided hereinafter.

NOT A COMMERCIAL WARRANTY

The following detailed description has been prepared solely to comply with the provisions of 35 U.S.C. §112, and does not constitute a commercial warranty (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of cherry tree, the following has been observed during the eleventh growing season, and under the ecological conditions prevailing at the orchard of the inventor which is located near Lodi, Calif. All major color code designations are by reference to The R.H.S. Colour Chart (Fourth Edition, 2001) provided by The Royal Horticultural Society of Great Britain. Common color names are also occasionally used.

DETAILED DESCRIPTION OF THE PREFERRED EMBODIMENTS

Tree:

*Size.*—Based upon the current age, and the rootstock employed, the observed tree is considered moderate in size, (10 feet tall, and 6.5' in diameter). All measurements have been taken from the originally discovered tree which is now 11 years old.

Vigor: Considered moderately high for the species.

Branching habit: Upright and spreading.

Branching strength: Considered medium.

Density: Considered moderately high.

Tree form: The present tree is trained to a modified, and open-vase form.

Hardiness: Considered hardy for Roosevelt, Wash. and Stockton, Calif.

Production: Considered moderate in precocity, and further produces flowers typically in year 3, and further produces about 40 pounds of fruit per tree in year 4.

Bearing: Annual.

Trunk: As measured at bloom time, the diameter of the tree when measured at a distance of about 30 cm above the ground is about 38.1 cm.

Bark texture: Smooth between lenticels.

Trunk color: Greyed-purple, (RHS 187A).

Lenticels:

*Generally.*—Numerous and prominent. Lenticel length, on average, is about 14.4 mm. Lenticel width, on average, is about 3.0 mm.

*Numbers of lenticels.*—The tree averages 7 to 9 lenticels per square centimeter.

*Lenticel color, center region.*—Grey-orange (RHS 175A), the outer color of the lenticel is white (RHS 156D).

Scaffold and second year fruiting branches: These branches have been measured at harvest maturity.

*Bark texture.*—Smooth and having numerous large lenticels.

*Branch size.*—Diameter as measured at a distance of 10-60 cm from the trunk union ranges from about 3 to about 6 cm. Crotch angles range from about 30 to 60 degrees when measured from the horizontal plane.

*Branch color.*—From the grey-purple group.

*Lenticels.*—Numbers — Numerous, and averaging 5 per sq. cm. Average lenticel length is about 0.3 mm; average lenticel width is less than about 0.3 mm. Lenticel color is grey-orange.

2nd year fruiting branches:

*Bark texture.*—Generally considered smooth.

*Branch diameter.*—This measurement ranges from about 6.5 mm to 9.4 mm when measured at the mid-point of growth.

*Branch color.*—Grey-orange (RHS 165A).

*Bark lenticels.*—Generally: Few in number, and averaging 7 per running cm of length; Lenticel shape — round, and ranging in size from 1.0 to 1.5 mm in diameter; Lenticel color grey-orange (RHS 164C).

Current year branches:

*Bark texture.*—Smooth.

*Branch size.*—The average length is about 45 cm, and the average width is about 6.5 mm when measured at a point about halfway along the length of the branch.

*Branch color.*—Brown (RHS 200C).

*Internode length.*—About 4.3 to 6.2 cm.

*Branch lenticels.*—Generally few in number, and averaging 5 per running cm; small in size, and round in shape, and ranging from 1.4-1.6 mm in diameter; Lenticel color is from the brown group (RHS N200D).

Flower buds: The following measurements are taken at full bud swell.

*Bud shape.*—Acute.

*Number of buds per fruiting spur.*—Variable from 3-7 per spur; the average bud length is about 8.3 mm; the average bud diameter is about 3.9 mm. The scale color is grey-purple (RHS 187A).

Leaves: Generally speaking, the following measurements have been taken from the midpoint of actively growing current season's growth at harvest maturity.

*Blade size.*—Considered large, and having an average length of 15.3 cm; a width of 7.3 cm; and a thickness of about 0.2 mm.

*Surface texture.*—Upper surface, considered smooth and leathery; Lower surface is considered smooth and leathery with a vein protruding above the surface.

*Leaf tip.*—Acuminate.

*Leaf base.*—Obtuse.

*Leaf form/shape.*—Elliptical.

*Leaf marginal edge.*—Shape: Mostly serrate, and occasionally doubly serrate.

*Blade color.*—Upper surface — green (RHS 136B); Lower surface color — green (RHS 138A).

*Midvein.*—Size — Considered large and averaging 1.2 mm in diameter when measured at the mid-point of the blade with a range of 1.0 to 1.4 mm. Color is yellow-green (RHS 147D).

*Petiole.*—Size — Averages 4.2 cm in length, and 2.1 mm in diameter when measured at the mid-point; upper surface color is from the greyed-orange group (RHS 176B); lower surface color is from the yellow-green group (RHS 147D). A 0.5 mm depth groove runs the full length of upper surface.

*Glands.*—Generally — Present, kidney shaped, and averaging 3.0 mm in length and 2.0 mm in width. Gland numbers range from 2-3, mostly two per petiole, and are further generally located about 0.5-1 cm from blade base with an occasional location just below the blade/petiole juncture. The glands are generally opposite in position; and the gland color is red-orange (RHS N34A).

Stipules: Not present.

Flowers: Generally: The bloom stands out, and typically does not drupe.

*First bloom.*—March 4-March 6 (3 year average). Full Bloom: March 14-March 16 (3 year average).

*Flower size.*—Generally: The bloom diameter, when fully open, averages about 43.7 mm, and is considered open.

*Bloom count.*—Numerous sprus are present on branches over two-years-old. Buds bearing flowers are numerous along the spurs and within each but there are typically a range of from 3-4 blossoms (flowers), per bud, and mostly 3.

Petals:

*Numbers.*—Five in number; petal color is white (RHS 155C), and occasionally somewhat translucent; petal size — average length is 16.5 mm; and the average width is 15.0 mm. Petal shape is round-conical; the base is rounded; and the apex is emarginate.

Nectary color: Yellow-green (RHS 154B).

Stamens:

*Filament.*—On average the number of filaments per bloom is 27; the filament color is white.

*Anther.*—Generally — Kidney shaped, and having an average size of 0.2 mm in width, and 0.6 mm in length.

Pollen:

*Generally.*—Abundant in quantity; the pollen color is grey-orange (RHS 163C).

Carpel:

*Styles.*—The average length is about 10.5 mm; Color is yellow-green (RHS 149D).

Stigma: Generally, considered oval in shape, and having an occasional indent on the upper surface. Average diameter of the stigma is 0.6 mm, and is yellow-green (RHS 149C).

Sepals: Generally: Five in number; deltoid in shape, laid back over the thalamus, and the tip is curled back towards petals when fully open; the average base width is 4.4 mm; the average length is 6.4 mm; the color is yellow-green (RHS 146C), with outside tip highlights having a greyed-red color (RHS 181A).

Peduncle: The average length is about 12.4 mm; the average diameter when measured at mid-length is 1.1 mm; and the color is yellow-green (RHS 144B).

Thalamus: The average depth is about 5.7 mm; the average width at the opening is about 3.9 mm; Urn shaped; and the color is yellow-green (RHS 144B).

Fruit:

*Harvest maturity.*—Harvest maturity is typically May 14-18, under the ecological conditions prevailing near Stockton, Calif., depending upon ambient environmental conditions.

Fruit size: Considered medium for the species. The average apical diameter is about 24.3 mm; and the average axial diameter is about 27.2 mm.

Fruit form: Generally oblate, and having uniform sides.

Fruit suture: This characteristic is very distinct on the back side, only, and is further mostly flush with the sides. Occasionally the suture is depressed by about 0.1-0.5 mm. The fruit suture width ranges from about 0.1 to 0.3 mm.

Fruit base: Flat with some variation to reniform in shape, and having a width which averages about 12.9 mm; and a depth which averages about 4.9 mm.

Fruit apex:

*Generally.*—Rounded, and ending in a slight depression of about 0.5 to 1.0 mm and which is marked by a russet dot that is about 1.0 to 1.5 mm in diameter.

Peduncle: The length ranges from 29.7 to 38.6 mm with an average length of about 33.6 mm; the peduncle diameter when measured at mid-point is about 1.5 mm; the peduncle color is green (RHS 138A).

Skin:

*Thickness.*—On average it is considered thin, about 0.05 to 0.08 mm.

Skin texture: The surface texture is smooth and clear, and melts in the mouth.

Lenticles, amount on fruit skin: Few.

Skin tenacity: Tenacious to the flesh. A thin layer of flesh is typically removed when the fruit is peeled.

Tendency to crack: Occasionally 2-10% cracking is observed following rain events.

Down: Wanting.

Color: Uniform and considered purple (RHS N77A).

Flesh:

*Color.*—Purple (RHS N79B).

Color of pit cavity: Purple (RHS N79B).

Flesh texture:

*Generally.*—Firm and lightly fibrous.

Fibers:

*Numbers.*—Moderate in number.

Pit tenacity: Considered moderate around the suture line, and light to non-existent elsewhere around pit.

Flesh ripening: Considered even.

Flesh flavor: Sweet and sub-acid.

Aroma: Very slight, and cherry-like.

Eating quality: Considered excellent.

Stone:

*Type*.—Considered a weak clingstone.

Stone size: Considered medium for the species. The average length 10.8 mm when measured between the base to apex; and about 7.4 mm wide when measured shoulder-to-shoulder. The stone is 9.3 mm wide when measured suture-to-suture.

Stone form: Narrowly elliptical.

Stone base:

*Shape*.—Rounded.

Stone apex:

*Shape*.—Rounded.

Stone sides:

*Generally*.—Considered equal.

Stone surface texture: Smooth.

Stone ventral edge: Generally: The suture is mostly sunken, and is subtended by two low ridges which converge basally and apically, and that averages 4.6 mm in width when measured at the mid-point. These ridges are again subtended by two partial ridges extending from the base to about ⅔ the distance to the apex, and about 2.4 mm in width when measured at the widest point.

Stone dorsal edge:

*Generally*.—This feature is a distinct, smooth, slightly raised ridge which extends from the base to apex, and which is further 0.4 mm high, and 0.2 mm wide.

Stone color: Gray-orange (RHS 165D).

Tendency to split: Not observed.

Kernel: Shape: Considered obtuse.

Kernel base:

*Shape*.—Rounded.

Kernel apex:

*Shape*.—Acute.

Kernel size: Generally the length ranges from 6.9 to 7.4 mm, with an average length of 7.1 mm. The width ranges from 4.4 to 5.0 mm with an average width of 4.7 mm. The kernel thickness ranges from 2.8 to 3.8 mm, with an average width of about 3.4 mm.

*Kernel color*.—Grey-orange (RHS 163A).

*Kernel taste*.—Bitter and almond like.

*Kernel viability*.—On average 11% of kernels did not develop. Viable kernel germination is presently unknown.

Use: An early season, premium, fresh market fruit.

Keeping quality: Acceptable for the species. The new variety's keeping quality is similar to the fruit produced by the 'Chelan' Cherry Tree. Cold storage of this fruit has been maintained at 33° F. for 10 days and longer.

Resistance to insects and diseases: The present variety shows no unusual susceptibility nor resistance to any diseases and/or plant or fruit pests which are common to sweet cherries that are found or grow in the States of California or Washington, respectively.

Shipping quality: Not thoroughly evaluated but the fruit appears suitable for shipments of 7-10 days in length assuming the fruit is treated with proper temperature and humidity controls.

Variance in botanical details: The present variety exhibits the above described characteristics when grown in the Stockton/Lodi region of California; and the Roosevelt, Wash. area of the United States. In Washington State, the fruit is often larger and free from all defects to a greater extent than that seen in California. A slight indentation in the suture line of the fruit may be exhibited in the fruit grown during some California growing seasons. This has not been observed in Washington State.

Fruit firmness: When measured at harvest maturity the present variety produced fruit having a value of 281. However fruit produced by the 'Chelan' Cherry Tree has a value of 290, and the fruit of the 'Brooks' Cherry Tree has a value of 272.

Brix: When measured at harvest maturity the fruit of the present variety had a brix of 20 when compared to the fruit of the 'Chelan' Cherry Tree (15); and the fruit of the 'Brooks' Cherry Tree (22).

Relative acidity: At harvest maturity the fruit of the new variety had an average acidic level, as compared to a high acidic value for the fruit of the 'Chelan' Cherry Tree; and a low acidic value for the fruit of the 'Brooks' Cherry Tree.

Relative fruit size: At harvest maturity, and when grown under similar ecologic conditions, the new variety produces fruit having a mean size 27 mm, as compared to the fruit of the 'Chelan' Cherry Tree (21.9 mm); and the 'Brooks' Cherry Tree (24.1).

Relative cracking: In comparison to the fruit produced by either the 'Chelan' or 'Brooks' Cherry Tree, the relative amount of cracking is lower, and is about 6%.

Although the new variety of cherry tree possesses the described characteristics when grown under the ecological conditions prevailing near Lodi and Stockton, Calif., it should be understood that variations of the usual magnitude, and characteristics incident to changes in growing conditions, fertilization, nutrition, pruning, pest control, frost, climate variables and changes in horticultural management are to be expected.

Having thus described and illustrated my new variety of cherry tree, what I claim as new and desire to secure by Plant Letters Patent is:

1. A new and distinct variety of sweet cherry tree, substantially as illustrated and described, what which is characterized by an early ripening fruit ('Chelan' timing), and which further has a large fruit, high production, self-fertility, a long stem and strong fruit attachment, and which further has a very attractive appearance, and organoleptic qualities.

* * * * *